(12) United States Patent
Bicer

(10) Patent No.: US 7,410,499 B2
(45) Date of Patent: Aug. 12, 2008

(54) VALVE HOLDER

(75) Inventor: Demetrio Bicer, Trabuco Canyon, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 106 days.

(21) Appl. No.: 11/102,345

(22) Filed: Apr. 8, 2005

(65) Prior Publication Data

US 2005/0228493 A1 Oct. 13, 2005

Related U.S. Application Data

(60) Provisional application No. 60/561,746, filed on Apr. 13, 2004.

(51) Int. Cl.
*A61F 2/24* (2006.01)

(52) U.S. Cl. ............... 623/2.11; 623/2.1; 623/2.18; 623/66.1; 606/139; 606/148

(58) Field of Classification Search ............... 623/2.11, 623/904, 2.1, 2.18; 606/99, 139, 148
See application file for complete search history.

(56) References Cited

U.S. PATENT DOCUMENTS 6,197,053 B1 * 3/2001 Cosgrove et al. ............ 623/2.11
2002/0133226 A1 * 9/2002 Marquez et al. ............ 623/2.11

* cited by examiner

*Primary Examiner*—William H. Matthews
*Assistant Examiner*—Suba Ganesan
(74) *Attorney, Agent, or Firm*—Barbara A. Wrigley; Oppenheimer Wolff & Donnelly LLP

(57) ABSTRACT

A valve holder assembly having a main valve holder and a detachable secondary valve holder for positioning a heart valve prosthesis.

18 Claims, 3 Drawing Sheets

VALVE HOLDER

REFERENCE TO RELATED APPLICATION

This application claims priority to Provisional Application Ser. No. 60/561,746 filed Apr. 13, 2004.

BACKGROUND OF THE INVENTION

1. Field of Application

This invention relates to devices and surgical procedures utilized for holding a stentless heart valve prosthesis during implantation.

2. Discussion of the Prior Art

Heart valve replacement is required when a patient's heart valve becomes diseased or damaged. Surgically-implanted hearted valve prostheses have extended the life expectancy of many patients who had defective natural valves. Such prostheses can be either mechanical or biological (mitral or aortic). The aortic prosthesis is implanted in the patient during a surgical procedure in which a segment of the aorta nearby the natural valve is slit open so that the malfunctioning valve can be removed and replaced with the prosthetic valve. The prosthetic valve must be held in place while the surgeon sutures or attaches the prosthetic heart valve to the annulus of the heart. Holding the implant in place while the surgeon places the sutures to attach it to the interior of the patient's aorta presents a difficult problem, due to the limited amount of space in the heart it is difficult to properly position and suturing the valve at the site of the annulus. To aid the surgeon during the implant procedure, it is known to use both disposable and non-disposable holders to position the valve during surgery. However, the known valve holders are large and cumbersome. These known valve holders are also unwieldy and obstruct the surgeon's view.

During this surgical procedure, the heart is typically stopped, and the patient put on heart/lung bypass. The longer a patient is required to rely on the artificial heart/lung bypass to maintain vital functions, the greater the stress on the patient. Thus there is a need to simplify the suturing of the heart valve prosthesis to the aorta in order to minimize both the length of surgery and the amount of time spent on heart/lung bypass.

Bioprosthesis from animal donors, such as those made of equine tissue, are flexible and are often supported by mechanical stents. A typical stented heart valve is disclosed in Duran, Reed Valve for Implantation into Mammalian Blood Vessels and Heart with Optional Temporary or Permanent Support, US 2005/0055079 A1. However, such stents occupy space within the aorta of the patients and may produce undesirable turbulence. Thus, there is a need to improve the suturing of a stentless heart valve prosthesis. Further, the positioning and alignment of the valve prosthesis to closely match that of the natural valve requires precision suturing.

The lack of a stent and easily pliable tissue material makes implantation of stentless valve difficult and time consuming. The stentless valves are very pliable and suturing and adequate positioning of the valve is very difficult. Several assistants are usually needed to holder the stentless valve in position with fingers, forceps or hemostats. This procedure is awkward for both the assistants and the surgeon performing the suturing. It is clearly advantageous to perform the valve surgery quickly as possible and to ensure symmetrical suturing and accurate placement of the prosthesis.

SUMMARY OF THE INVENTION

The invention relates to an improved valve holder assembly to position and hold a stentless valve prosthesis. A suitable stentless heart valve prosthesis is that of Myers et al., Prosthetic Heart Valve, U.S. Pat. No. 6,682,559, hereby incorporated by reference. The valve holder assembly has a main valve holder that is open and generally cylindrical. This main valve holder has a top member, adapted to receive a handle, a generally cylindrical main valve holder ring base, and support members connecting the top and base. The valve holder assembly further includes a removable secondary valve holder that includes three collapsible commissural posts radiating outwardly. The secondary valve holder is adapted to nest within the hollow space of the main valve holder and has substantially the same centerline as the main valve holder. The secondary valve holder has a top member allowing for removably connecting the secondary valve holder to the main valve holder. The invention includes a rigid, hollow, generally cylindrical and open main valve holder having a top member adapted to receive a main valve holder handle, a generally cylindrical main valve holder ring base, and support members connecting the main valve holder top member and the ring base, the main valve holder adapted to hold a prosthetic valve. A removable secondary valve holder nests within the hollow space of the generally cylindrical main valve holder and has substantially the same centerline as the main valve holder. The secondary valve holder includes a flat, disc-shaped secondary valve holder top member removably connected to the main valve holder top member; a rotational axel coupled to said secondary valve holder top member; and three elongated commissural posts extending radially from said top member and rotational axel along a substantially horizontal axis thereof. The commissural posts are structured to collapse from a position along the horizontal axis to a position along a substantially vertical axis. The commissural posts are adapted to position the prosthetic valve during surgical implantation.

The invention provides a valve holder assembly that is securely attached to a prosthetic valve and allows the surgeon or surgeon assistants to easily manipulate the valve holder assembly so that the inflow portion of the suture ring of the replacement valve is properly aligned with the aortic annulus and to ensure symmetrical suturing and accurate placement of the prosthesis commissural post tabs to the aortic wall. First, the surgeon loosely sutures the suture ring of the replacement valve to the aortic annulus and then can lower the valve with the holder into the aortic wall to the aortic annulus. Next, the main valve holder is then detached from the prosthetic valve by easily pulling away cutting the temporary assembling sutures from the attached prosthetic heart valve, leaving the secondary holder in place attached to the valve from the three prosthesis commissural suture tabs. Next, the retractable holder is collapsed. As a result, the suture ring of the prosthetic heart valve is sutured into the aortic annulus and remains unobstructed to the surgeons to tie the sutures. Next, the retractable secondary holder is pulled up in a straight line and the valve is aligned with the suture tabs in symmetrical suturing placement. The commissural tabs are released by cutting the assembling sutures from the secondary holder one by one and sewn to the aortic wall. Finally, the secondary retractable holder is released and removed from surgical field. An alternative to the last step is to do the first suture to the top of each of the suture tabs, release the secondary holder and then finish the suturing as necessary.

With the utilization of the above mentioned instrument, surgical procedures involving the implant of stentless heart valves are less complicated and can be performed faster.

DESCRIPTION OF THE PREFERRED EMBODIMENTS

Figure 1:
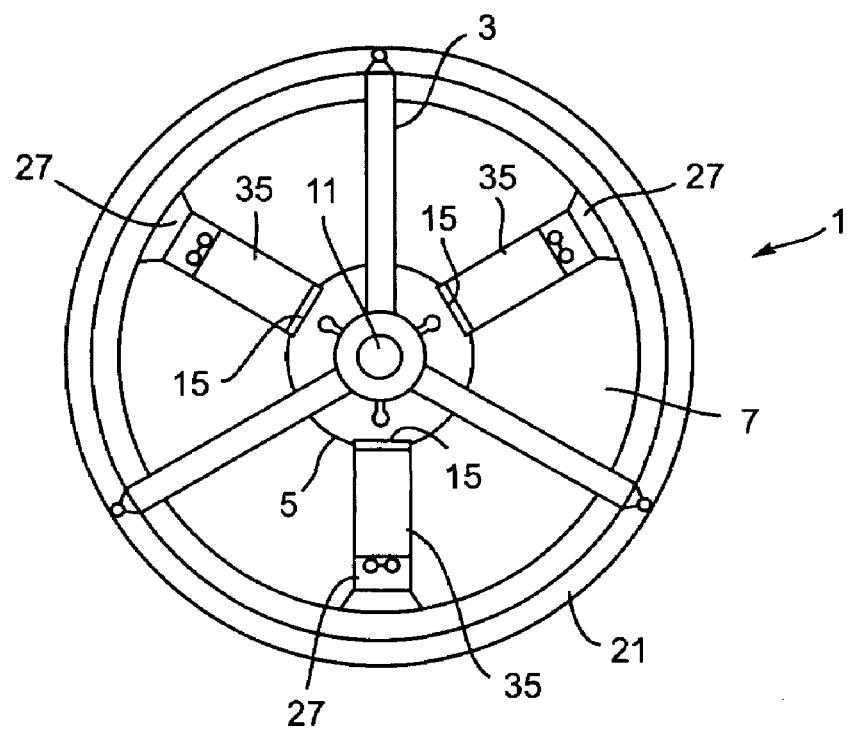
FIG. 1 is a top view of the valve holder assembly.
Figure 2:
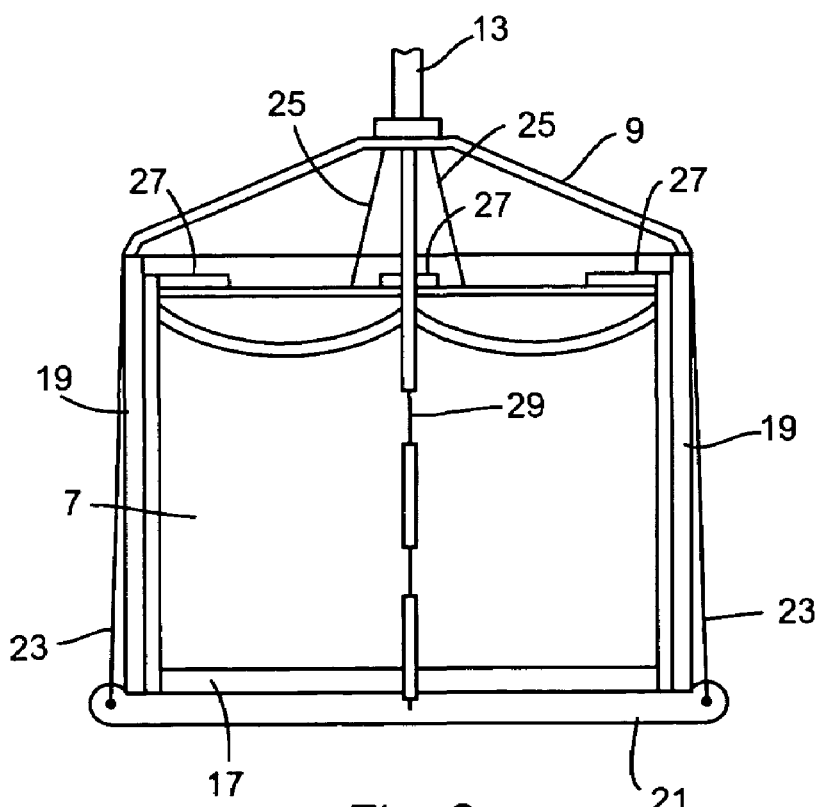
FIG. 2 is a side view of the valve holder assembly.

As shown in FIG. 1 and FIG. 2, the present invention is directed to a valve holder assembly 1, having a main valve holder 3 and a retractable or removable secondary valve holder 5 within which is positioned a stentless heart valve prosthesis 7. The main valve holder 3 is generally cylindrical and open or hollow with a main valve holder top member 9, adapted at hole 11, preferably threaded, to receive a handle 13 as shown in FIG. 2. The main valve holder 3 has narrow strut support members 19. Preferably, the main valve holder base 17 is scalloped as the valve of U.S. Pat. No. 6,682,559 is scalloped. The stentless prosthetic heart valve 7 includes a prosthetic heart valve suture ring 21 to which main valve holder assembly sutures 23 may be used to secure the prosthetic heart valve suture ring 21 to the main valve holder 3. Further, secondary holder valve assembling sutures 25 may be employed to secure the main valve holder 3 to the secondary valve holder 5.

Figure 3:
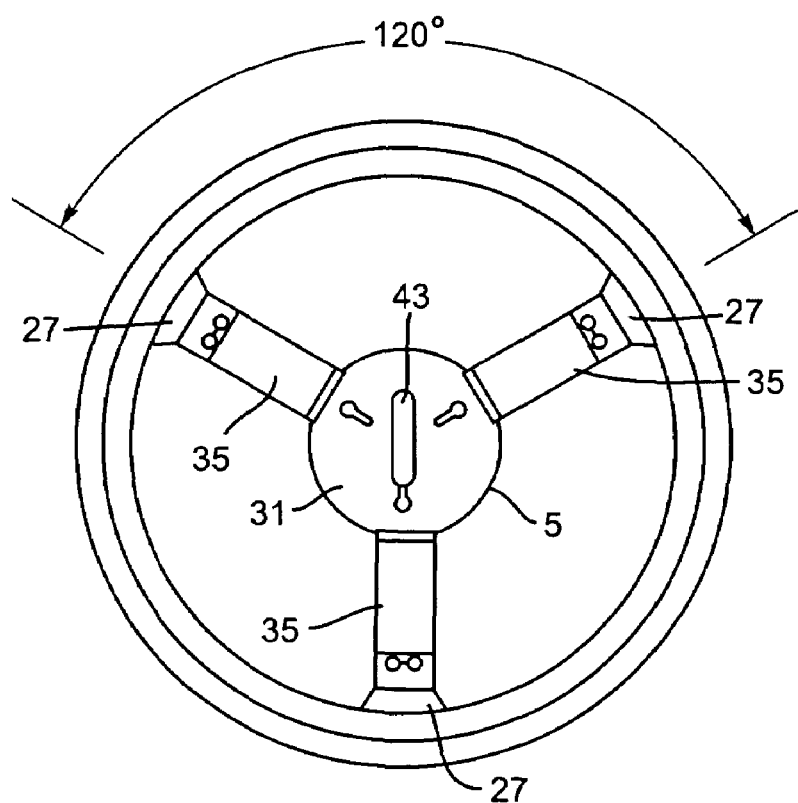
FIG. 3 is a top view of the secondary valve holder with a heart valve prosthesis mounted therewithin.

The heart valve prosthesis 7 includes commissural valve tabs 27 secured to the secondary heart valve holder 5. As shown in FIG. 1 and FIG. 2, the main valve holder 3 and the secondary valve holder 5 have substantially the same centerline 29. And the secondary valve holder 5 is adapted to removably nest within the main valve holder 3. As shown in FIGS. 1, 2 and 3 the heart valve prosthesis 7 includes a rigid, hollow, generally cylindrical and open main valve holder 3 having a top member 9 adapted to receive a main valve holder handle 13, a generally cylindrical main valve holder ring base 17, and support members connecting the main valve holder top member and the ring base 19. The main valve holder 3 is adapted to hold a prosthetic valve 7. A removable secondary valve holder 5 nests within the hollow space of the generally cylindrical main valve holder 3 and has substantially the same centerline as the main valve holder 3. The secondary valve holder 5 includes a flat, disc-shaped secondary valve holder top member 31 removably connected to the main valve holder top member 9; a rotational axel 15 coupled to said secondary valve holder top member 31; and three elongated commissural posts 35 extending radially from said top member 31 and rotational axel 15 along a substantially horizontal axis thereof. The commissural posts 35 are structured to collapse from a position along the horizontal axis to a position along a substantially vertical axis.

Figure 4:
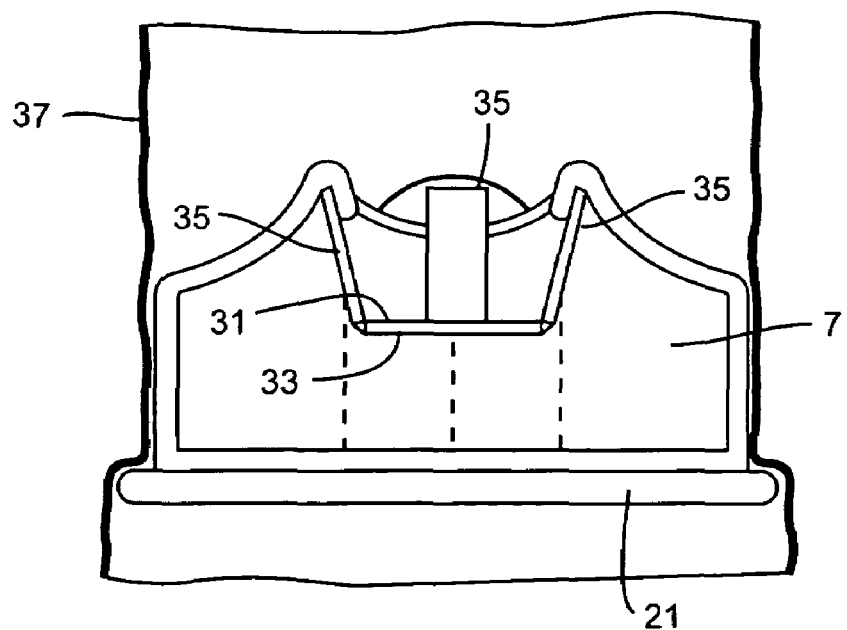
FIG. 4 is a slide view of the valve, already sutured to the aortic annulus and partially collapsed secondary valve holder.

Turning now to FIG. 3 and FIG. 4, the secondary valve holder 5 has a secondary valve top member 31 and three collapsible commissural posts 35 preferably spaced 120° from each other and adapted to flex about rotational axle 15. In FIGS. 3 and 4, the main valve holder 3 has been removed. FIG. 4 shows the secondary valve holder 5 and the stentless heart valve prosthesis 7 in the partially collapsed position.

Figure 5:
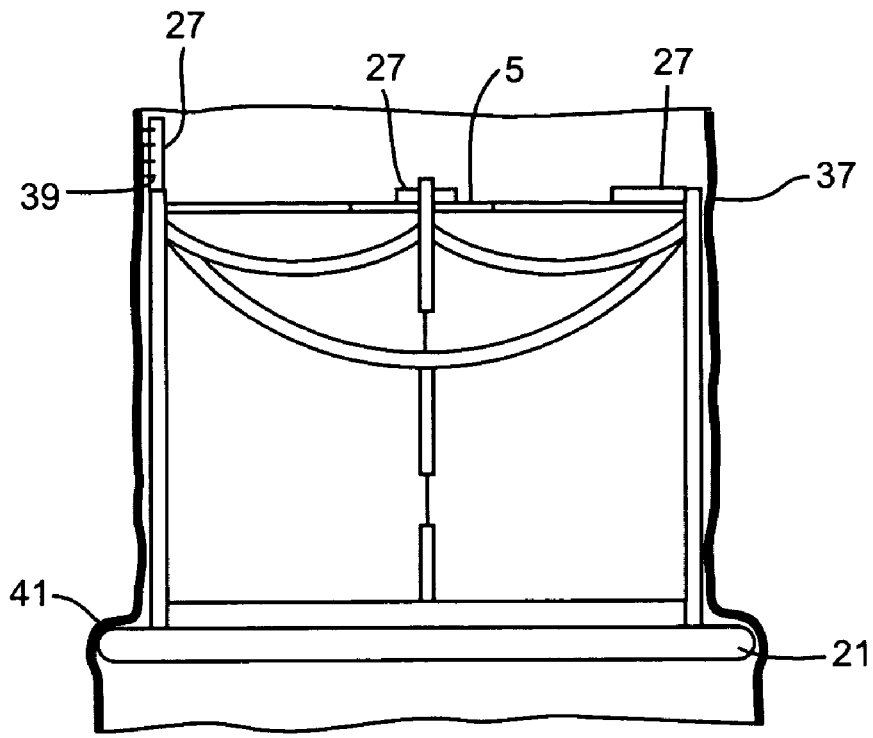
FIG. 5 is a side view of the fully extended secondary valve holder and stentless heart valve prosthesis along the aortic wall.

FIG. 5 shows the secondary valve holder 5 in its extended or non-collapsed position. The commissural post valve tabs 27 can be sutured to the aortic wall 37 by means of sutures 39.

Figure 6:
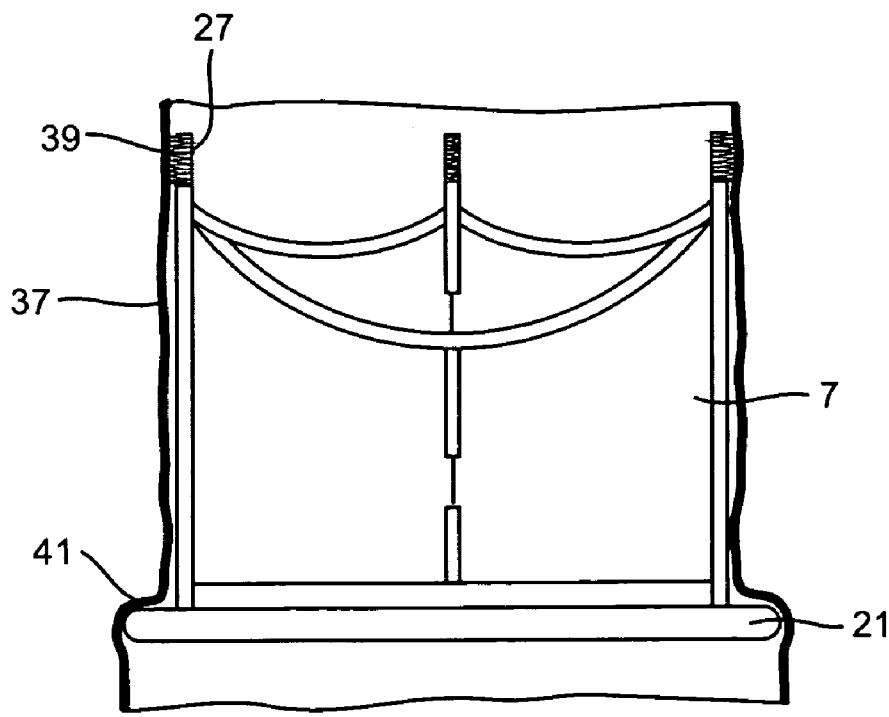
FIG. 6 is a side view of a stentless heart valve prosthesis sutured to the aortic annulus, the commissural post tabs sutured to the aortic wall and the secondary valve holder removed.

FIG. 6 shows the stentless heart valve prosthesis 7 sutured to the aortic wall 37, with the secondary valve holder 5 removed, and the suture ring sutured to the aortic annulus 41.

Having described the structure of the valve holder of this invention, its method of use will now be discussed.

The valve holder assembly 1, including main valve holder 3, secondary valve holder 5 and stentless heart valve prosthesis 7 is employed for implantation as shown in FIG. 1 and FIG. 2 following removal of a patient's diseased or damaged natural heart valve. FIG. 4-FIG. 6 illustrates the implantation of the stentless heart valve prosthesis 7 after suturing the valve suture ring 21 to the aortic annulus 41, and removal of the main valve holder 3 by cutting main valve holder assembling sutures 23. FIG. 4 illustrates the secondary valve holder 5 and the stentless heart valve prosthesis 7 in the partially collapsed position, allowing the surgeon or technician to tie the suture of the stentless heart valve prosthesis suturing 21 to the aortic annulus 41. Secondary valve holder 5 may be collapsed by pressing secondary valve holder handle 43.

FIG. 5 illustrates the secondary valve holder 5 in the uncollapsed or fully extended implanting position, and one of the three commissural valve tabs 27 removed from the secondary valve holder 5 and sutured to the aortic wall 37. Finally, in FIG. 6, the commissural valve tabs 27 have been sutured to the aortic wall 37, and the secondary valve holder 5, that in effect acts as a temporary stent during the implantation procedure only, removed.

The holder of the present invention may be made of metal or other plastic materials that can be cleaned or sterilized in an autoclave, as it is well known by those skilled in the art. In another embodiment, the holder is made of plastic and, thus be disposable. Obviously, numerous variations and modifications can be made within departing from the spirit of the present invention. Therefore, it should be clearly understood that the forms of the present invention described above and shown in the figures of the accompanying drawings are illustrative only and are not intended to limit the scope of the present invention.

The invention claimed is:

1. A valve holder assembly comprising:
a rigid, hollow, generally cylindrical and open main valve holder having a top member adapted to receive a main valve holder handle, a generally cylindrical main valve holder ring base, and support members connecting the main valve holder top member and the ring base, the main valve holder adapted to hold a prosthetic valve; and
a removable secondary valve holder nested within the hollow space of the generally cylindrical main valve holder and having substantially the same centerline as the main valve holder, said secondary valve holder comprising:
a flat, disc-shaped secondary valve holder top member removably connected to the main valve holder top member;
a rotational axle coupled to said secondary valve holder top member;
three elongated commissural posts extending radially from said top member and rotational axle along a substantially horizontal axis thereof, said commissural posts structured to collapse from a position along said horizontal axis to a position along a substantially vertical axis and adapted to position the prosthetic valve during surgical implantation.

2. The valve holder assembly of claim 1, further comprising a stentless heart valve prosthesis positioned within the secondary valve holder.

3. The valve holder assembly of claim 2, further comprising a stentless aortic heart valve prosthesis having a suturing ring.

4. The valve holder assembly of claim 1, wherein the secondary valve holder is attachable to the main valve holder with one or more sutures.

5. The valve holder assembly of claim 1, wherein the main valve holder and the secondary valve holder are formed from metal.

6. The valve holder assembly of claim 1, wherein the main valve holder and the secondary valve holder are formed from plastic.

7. A valve holder assembly for holding and positioning a prosthetic valve during surgical implantation comprising:
   a generally cylindrical main valve holder having a top member, a ring base, and a plurality of support members extending between the main valve holder top member and the ring base, the main valve holder adapted to hold the prosthetic valve; and
   a secondary valve holder configured to removably nest within the main valve holder, the secondary valve holder comprising:
      a substantially flat, disc-shaped top member;
      a rotational axle coupled to said secondary valve holder top member;
      a plurality of elongated commissural posts extending radially from the top member and the rotational axle along a substantially horizontal axis thereof, said commissural posts structured to collapse from a position along said substantially horizontal axis to a position along a substantially vertical axis and adapted to position the prosthetic valve during surgical implantation.

8. The valve holder assembly of claim 7, wherein the top member of the main valve holder further comprises an aperture adapted to receive a handle.

9. The valve holder assembly of claim 7, wherein the secondary valve holder is securable to the main valve holder with one or more sutures.

10. The valve holder assembly of claim 7, wherein the prosthetic valve is a stentless heart valve prosthesis.

11. A valve holder assembly comprising:
   a first generally cylindrical valve holder having a top member, a generally cylindrical ring base, a hollow body portion, and a plurality of strut support members surrounding the hollow body portion, each strut support member coupled on a first end to the first valve holder top member and on a second end to the generally cylindrical ring base;
   a second valve holder having a substantially similar centerline to the first valve holder and configured to removably nest within the hollow body portion of the first valve holder, the second valve holder adapted to be sutured to the first valve holder and comprising;
   a substantially flat, disc-shaped secondary valve holder top member;
   a plurality of elongated commissural posts extending radially from said top member along a substantially horizontal axis thereof, said plurality of elongated commissural posts structured to collapse from a position along said horizontal axis to a position along a substantially vertical axis and adapted to position the prosthetic valve during surgical implantation; and
   a prosthetic valve configured to be implanted in a heart, the prosthetic valve having a suture ring and a plurality of commissural valve tabs, wherein the suture ring is adapted to be sutured to the first valve holder and the valve tabs are adapted to be sutured to the plurality of elongated commissural posts of the second valve holder during implantation of the prosthetic valve.

12. The valve holder assembly of claim 11, wherein the second valve holder has three commissural posts.

13. The valve holder assembly of claim 12, wherein the commissural posts are spaced about 120 degrees from one another.

14. The valve holder assembly of claim 11, wherein the commissural tabs of the prosthetic valve are structured for attachment to an aortic wall of the heart.

15. The valve holder assembly of claim 14, wherein the suture ring of the prosthetic valve is structured for attachment to an aortic annulus of the heart.

16. The valve holder assembly of claim 11, wherein the top member of the first valve holder comprises an aperture adapted to receive a handle.

17. The valve holder assembly of claim 16, wherein the aperture and the handle are threaded.

18. The valve holder assembly of claim 11 wherein said secondary valve holder includes a secondary valve holder handle operably coupled to said secondary valve holder top member for removably collapsing said secondary valve holder.

* * * * *